United States Patent
Widmann (10) Patent No.: US 10,660,964 B2
(45) Date of Patent: May 26, 2020

(54) PHARMACEUTICAL COMPOSITION FOR THE PARENTERAL ADMINISTRATION OF ULTRASHORT-EFFECTIVE BETA-ADRENORECEPTOR ANTAGONISTS

(71) Applicant: AOP ORPHAN PHARMACEUTICALS AG, Vienna (AT)

(72) Inventor: Rudolf Stefan Widmann, Purkersdorf (AT)

(73) Assignee: AOP Orphan Pharmaceuticals AG, Vienna (AT)

( * ) Notice: Subject to any disclaimer, the term of this patent is extended or adjusted under 35 U.S.C. 154(b) by 0 days.

(21) Appl. No.: 16/164,926

(22) Filed: Oct. 19, 2018

(65) Prior Publication Data

US 2019/0046646 A1 Feb. 14, 2019

Related U.S. Application Data

(63) Continuation of application No. 15/248,845, filed on Aug. 26, 2016, now abandoned, which is a continuation of application No. 12/809,927, filed as application No. PCT/AT2008/000470 on Dec. 22, 2008, now abandoned.

(30) Foreign Application Priority Data

Dec. 21, 2007 (AT) .................................. 2107/2007

(51) Int. Cl.
| | |
|---|---|
| *A61K 47/40* | (2006.01) |
| *A61K 9/00* | (2006.01) |
| *A61K 31/24* | (2006.01) |
| *A61K 31/5377* | (2006.01) |
| *A61K 31/724* | (2006.01) |
| *B82Y 5/00* | (2011.01) |
| *A61K 47/69* | (2017.01) |

(52) U.S. Cl.
CPC ............ *A61K 47/40* (2013.01); *A61K 9/0019* (2013.01); *A61K 31/24* (2013.01); *A61K 31/5377* (2013.01); *A61K 31/724* (2013.01); *A61K 47/6951* (2017.08); *B82Y 5/00* (2013.01)

(58) Field of Classification Search
CPC ............... A61K 2300/00; A61K 31/24; A61K 31/5377; A61K 31/724; A61K 47/40; A61K 47/48969; A61K 9/0019; B82Y 5/00

See application file for complete search history.

(56) References Cited

U.S. PATENT DOCUMENTS

| | | | |
|---|---|---|---|
| 5,017,609 | A | 5/1991 | Escobar et al. |
| 2003/0216349 | A1 | 11/2003 | Belardinelli et al. |
| 2004/0053894 | A1 | 3/2004 | Mazess et al. |
| 2008/0293810 | A1 | 11/2008 | Tiwari et al. |

FOREIGN PATENT DOCUMENTS

| | | |
|---|---|---|
| CN | 1827109 | 9/2006 |
| DE | 4207922 | 9/1993 |
| EP | 0403578 | 12/1990 |
| EP | 1417962 | 5/2004 |
| JP | H03-500658 | 2/1991 |
| JP | H08-503951 | 4/1996 |
| JP | 2004-519506 | 7/2004 |
| JP | 2005-530736 | 10/2005 |
| WO | WO 85/004580 | 10/1985 |
| WO | WO 94/012217 | 12/1993 |
| WO | WO 02/076446 | 10/2002 |
| WO | WO 03/028718 | 4/2003 |
| WO | WO 03/033025 | 4/2003 |
| WO | WO 2007/012974 | 2/2007 |

OTHER PUBLICATIONS

Baaske et al., "Stability of esmolol hydrochloride in intravenous solutions," *Am. J. Hops. Pharm.*, 1994, 51:2693-2696.
Ikeda et al., "NMR Spectroscopic Characterization of Metoprolol/Cyclodextrin Complexes in Aqueous Solution: Cavity Size Dependency," *Journal of Pharmaceutical Sciences*, 2004, 92:1659-1671.
International Preliminary Report on Patentability for PCT/AT2008/000470, dated Aug. 3, 2010.
Loftsson et al., "Cyclodextrins in drug delivery," *Expert Opin. Drug Deliv.*, 2005, 2:335-351.
Mio, "New ultra-short-acting beta-blockers: landiolol and esmolol—the effects on cardiovascular system," *Masui*, 2006, 55(7): 841-848. (English Abstract).
Pitha et al., "Drug Solubilizers to Aid Pharmacologists: Amorphous Cyclodextrin Derivatives," *Life Sciences*, 1988, 43:493-502.
Rajewski et al., "Pharmaceutical Applications of Cyclodextrins. 2. In Vivo Drug Delivery," *Journal of Pharmaceutical Sciences*, 1996, 85(11):1142-1169.
Ren et al., "Separation of Chiral Basic Drugs with Sulfobutyl-β-Cyclodextrin in Capillary Electrophoresis," *Chromatographia*, 1999, 50(5/6):363-368.
Rosenberg et al., "An Accurate Prediction of the pH Change Due to Degradation: Correction for a 'Produced' Secondary Buffering System," *Pharmaceutical Research*, 1988, 5(8):514-517.

(Continued)

*Primary Examiner* — Jean P Cornet
(74) *Attorney, Agent, or Firm* — Norton Rose Fulbright US LLP (57) ABSTRACT

The present invention relates to a pharmaceutical composition in the form of a storage-stable solution for the parenteral administration of ultrashort-effective β-adrenoreceptor antagonists, comprising a) an ultrashort-effective β-adrenoreceptor antagonist and/or a pharmaceutically acceptable salt thereof, b) water, and c) a cyclodextrin and/or a functional cyclodextrin derivative. The composition according to the invention has high stability, even without the presence of additional adjuvants.

8 Claims, 9 Drawing Sheets

(56) References Cited

OTHER PUBLICATIONS

Wiest et al., "Stability of esmolol hydrochloride in 5% dextrose injection," *Am J Helth-Syst Pharm*, 1995, 52:716-718.
Yasuda et al., "Ultra-short-acting cardioselective beta-blockage attenuates postischemic cardiac dysfunction in the isolated rate heart," *European Journal of Cardio-thoracis Surgery*, 2001, 19:647-652.

PHARMACEUTICAL COMPOSITION FOR THE PARENTERAL ADMINISTRATION OF ULTRASHORT-EFFECTIVE BETA-ADRENORECEPTOR ANTAGONISTS

CROSS-REFERENCE TO RELATED APPLICATIONS

The present application is a continuation of U.S. patent application Ser. No. 15/248,845, filed Aug. 26, 2016, which is a continuation of U.S. patent application Ser. No. 12/809,927, filed Aug. 19, 2010, which is a national phase application under 35 U.S.C. § 371 of International Application No. PCT/AT2008/000470, filed Dec. 22, 2008, which claims priority to Austrian Patent Application No. A2107/2007, filed Dec. 21, 2007.

BACKGROUND

1. Field of the Invention

The present invention relates to a pharmaceutical composition for parenteral administration of an ultrashort-effective β-adrenoreceptor antagonist in the form of a solution.

2. Description of Related Art

Due to their very short elimination half-life, ultrashort-effect β-adrenoreceptor antagonists such as esmolol hydrochloride, landiolol hydrochloride (two cardioselective $β_1$ blockers) and flestolol hydrochloride are used in the form of parenteral formulations, particularly in anaesthesia and in emergency and intensive care medicine.

For the purpose of this invention, the term "ultrashort-effective" is taken to mean an active substance with an elimination half-life which is less than that of the $β_1$ blocker metoprolol (half-life $t_{1/2}$=90 minutes). More particularly, the elimination half-life of the β-adrenoreceptor antagonists used in accordance with the invention is preferably less than 20 minutes.

One problem is the low stability of these active substances in aqueous solution as they are hydrolytically split into free acids and alcohol (in the case of esmolol into pure acid and methanol) [e.g. Baaske D M, Dykstra S D, Wagenknecht D M, Karnatz N N Stability of esmolol hydrochloride in intravenous solutions. Am J Hosp Pharm. 1994 Nov. 1; 51 (21): 2693-6; Tamotsu Yasuda, Hiroyuki Kamiya, Yoko Tanaka, Go Watanbe, Ultrashort-acting cardioselective beta-blockade attenuates postischemic cardiac dysfunction in the isolated rat heart. Eur J Cardiothorac Surg 2001; 19:647-652].

On the other hand the active substance concentration of, for example esmolol, used for administration is so high that these solutions are often hypertonic. In addition, to stabilise these solutions alcohol in concentrations of around 25% is added in many cases. Because of these technical formulation problems, the use of esmolol in intensive care medicine is associated with additional risks.

Commercially obtainable landiolol is, for example, currently only available in fixed formulations which have to be dissolved before being used in intensive care medicine, leading to an unnecessary loss of time. Freeze-dried compositions containing landiolol are known from CN 1827109A.

Attempts to solve the problems cited for esmolol include the addition of dextrose [Wiest D B, Garner S S, Childress L M., Stability of esmolol hydrochloride in 5% dextrose injection. Am J Health Syst Pharm 1995 Apr. 1; 52 (7) 716-8.], adjusting the pH value to <6 [Rosenberg L S, Hostetler C K, Wagenknecht D M, Aunet D A., An accurate prediction of the pH changes due to degradation: correction for a "produced" secondary buffering system. Pharm. Res. 1988 August; 5(8): 514-7.], as well as the addition of propylene glycol in high concentrations [http://www.rxlist.com/cgi/generic3/esmolol.htm].

WO 85/04580 describes solutions of esmolol in a proportion by weight of 0.1% to 30% which also include a buffer and ethanol in a proportion of 5 to 60%.

In its claim 1, EP 0403578 claims an injectable, aqueous composition for treating heart conditions, which has an effective quantity of esmolol (hydrochloride) in a proportion of 1 mg to 250 mg esmolol/ml solution and 0.01 to 0.04 M buffer, and has a pH value in the range 4.5 to 5.5.

International publication WO 02/076446 describes an esmolol solution containing 0.1 to 500 mg/ml esmolol hydrochloride, 0.01 to 2 M buffer and 1 to 500 mg/ml of an osmosis-adjusting agent.

European publication EP 1417962 describes pharmaceutical compositions consisting of 30 ml to 70 ml dilution with an proportion of 1500 mg to 3500 mg esmolol or a pharmaceutically tolerable salt thereof.

SUMMARY

There are no known attempts to solve the cited problem for landiolol.

The aim of the present invention is to provide a composition for parenteral administration of ultrashort-effective β-adrenoreceptor antagonist, more particularly for injection or infusion, which on the one hand exhibits a high degree of storage stability and on the other hand an osmolarity which is suitable for administration. The composition should exhibit vaso-protective properties, which is important especially at high active substance concentrations (e.g., in the case of esmolol).

Surprisingly it was found that the use of a cyclodextrin and/or a functional cyclodextrin derivative to increase the stability of an ultrashort-effective β-adrenoreceptor antagonist and/or a pharmaceutically acceptable salt thereof in a suitable storage-stable aqueous solution for parenteral administration fulfils the aim of the invention in an excellent manner.

In this aspect of the present invention the solution can also contain other auxiliary substances, in particular buffers, preservation agents, organic solvents that can be mixed with water, salts, sugar alcohols and/or sugar.

A further aspect of the present invention relates to a pharmaceutical composition for parenteral administration of an ultrashort-effective β-adrenoreceptor antagonist in the form of a storage-stable solution, essentially consisting of a) an ultrashort-effective β-adrenoreceptor antagonist and/or a pharmaceutically acceptable salt thereof b) water and c) a cyclodextrin and/or a functional cyclodextrin derivative DE 4207922 and US 2004/0053894 describe in general the use of cyclodextrin in pharmaceutical compositions. The use of cyclodextrin in pharmaceutical compositions is also described in WO 2003/033025, US 2003/021349 and in Ikeda et al., J. Pharm Sci. 2004, 93(7), 1659-1671.

It was found that by adding cyclodextrin and/or a functional cyclodextrin derivative, the stability of ultrashort-effective β-adrenoreceptor antagonists in pure aqueous solutions can be decisively increased.

Surprisingly, ultrashort-effective β-adrenoreceptor antagonist solutions consisting solely of the ultrashort-effective β-adrenoceptor antagonist, cyclodextrin and water, are sufficiently storage-stable, even without the presence of other auxiliary substances (such as buffer or osmolarity-adjusting agents known from the prior art) and, in terms of osmolar properties are suitable for administration. This applies particularly in the pH range from 3 to 7.5, preferably from 5 to 7.

For the purpose of the present invention the term "storage-stable" denotes an aqueous solution, which in contrast to a solution produced through the dissolution of freeze-dried products, can be stored for a longer period of time without any significant breakdown of the contained active substance taking place. Understood as "storage-stable" in particular are aqueous solutions in which after one month less than 5% of the active substance has degraded.

As has been stated above, the pH value of the solution is preferably 3 to 7.5, particularly preferably 5 to 7.

The concentration of the cyclodextrin or cyclodextrin derivative in the solution is preferably 0.1% to 20% (w/v), preferably 0.25% to 7% (w/v), particularly preferably 0.5% to 4%.

The cyclodextrin or the functional cyclodextrin derivative is preferably selected from the group comprising α-cyclodextrin, β-cyclodextrin, γ-cyclodextrin, functional derivatives and mixtures thereof.

"Functional cyclodextrin derivatives" is taken to mean all pharmaceutically acceptable derivatives of cyclodextrins in which the essential structure and size of the cyclodextrin molecules are retained. Considered as functional cyclodextrin derivatives in particular are esters with pharmaceutically acceptable acids and ethers, especially low-alkyl ethers. Particularly preferred cyclodextrin derivatives are (2-hydroxypropyl)-β-cyclodextrin and (sulfobutylether)-7β-cyclodextrin.

The ultrashort-effective β-adrenoreceptor antagonist used in the composition in accordance with the invention is preferably an active substance selected from the group comprising esmolol, landiolol and flestolol.

The concentration of the ultrashort-effective β-adrenoreceptor antagonist or the salt therefore in the solution can be 0.1% to 30% depending on the β-adrenoreceptor antagonist used. Preferred concentrations in the case of esmolol or esmolol salts are 1 to 20%. Preferred concentrations in the case of landiolol or laniolol salts are 1 to 20%. Preferred concentrations in the case of flestolol or flestolol salts are 0.1 to 10%.

The solution preferably has an osmolarity of 270 mosmol/l to 310 mosmol/l, particularly preferably 280 mosmol/l to 300 mosmol/l. This corresponds to an isotonic solution.

In the case of esmolol the composition in accordance with the invention is preferably present in the form of a sales unit selected from the group comprising:
  1 ml solution containing 10-20 mg esmolol or a salt thereof
  2 ml solution containing 10-100 mg esmolol or a salt thereof
  5 ml solution containing 50-500 mg esmolol or a salt thereof
  10 ml solution containing 50-5000 mg, more particularly 2500 mg esmolol or a salt thereof
  50 ml solution containing 50-5000 mg esmolol or a salt thereof [0034] 100 ml solution containing 50-5000 mg esmolol or a salt thereof
  250 ml solution containing 50-5000 mg esmolol or a salt thereof.

In the case of conventional products a 10 ml solution containing 100 mg esmolol as a "ready-to-use" product can be used directly for injection. Conventional compositions with high proportions of esmolol (more particularly 10 ml/2500 mg esmolol) must be diluted before administration. In comparison, due to their vasoprotective properties, solutions in accordance with the invention can also be used with higher concentrations of esmolol as "ready-to-use" products.

In the case of landiolol and/or festolol the composition according to the invention is preferably available in the form of a sales unit selected from the group comprising
  1 ml solution containing 5-20 mg landiolol or festolol or a salt thereof
  2 ml solution containing 5-100 mg landiolol or festolol or a salt thereof
  5 ml solution containing 10-500 mg landiolol or festolol or a salt thereof
  10 ml solution containing 10-5000 mg landiolol or festolol or a salt thereof
  25 ml solution containing 25-2500 mg landiolol or festolol or a salt thereof
  50 ml solution containing 50-5000 mg landiolol or festolol or a salt thereof
  100 ml solution containing 50-5000 mg landiolol or festolol or a salt thereof
  250 ml solution containing 50-5000 mg landiolol or festolol or a salt thereof.

In conventional products containing landiolol, 50 mg of landiolol is contained as dry substance. These products must first be made into a solution before injection.

In the compositions of landiolol according to the invention, the landiolol is already present in solution in a stable form. In general, due to the vasoprotective properties of the compositions according to the invention, comparatively higher concentrations of the ultrashort-effective β-adrenoreceptor antagonists than in the formulations to date can be used.

The composition according to the invention can be produced in a known manner through mixing and subsequent dissolution of the constituents.

The composition according to the invention can be used in particular to produce a medicinal product to reduce ventricular frequency in patients with atrial fibrillation, atrial flutter and sinus tachycardia, in atrioventricular and AV node tachycardia, tachycardic supra- and ventricular arrhythmias, in tachycardia and/or hypertension, before, during and after operations as well as in other emergency situations, for the prophylaxis and treatment of perioperative ischaemia, to treat unstable angina pectoris and acute myocardial infarction.

BRIEF DESCRIPTION OF DRAWINGS

The invention will be explained in more detail below with the aid of examples of embodiment and figures.

DETAILED DESCRIPTION

Example 1

Production of (2-hydropropyl)-β-cylodextrin-esmolol Complexes

An equimolar quantity of (2-hyroxypropyl)-β-cyclodextrin was added to a 5% esmolol solution and stirred for 6 hours.

Example 2

Production of α- and γ-cyclodextrin-esmolol Complexes

An equimolar quantity of α-cyclodextrin (Cavamax W6 Pharma, manufacturer Wacker Chemie AG) (example 2a) or γ-cyclodextrin (Cavamax W8 Pharma, manufacturer Wacker Chemie AG) example 2b) was added to a 5% esmolol solution and stirred for 18 hours.

Example 3

Production of Cyclodextrin-Esmolol Complexes

Example 3a

Esmolol and α-cyclodextrin are dissolved in final concentrations of 5% (w/v) (esmolol) and 14% (w/v) α-cyclodextrin) in water for injection purposes and stirred for 24 hours at room temperature.

Example 3b

Esmolol and optionally additionally α-cyclodextrin are dissolved in a final concentration of 5% (w/v) (esmolol) or 14%, 7%, 4%, 2%, 1% and 0% (w/v) (α-cyclodextrin) in water for injection purposes and stirred for 24 hours at room temperature.

Example 3c

Esmolol and optionally additionally hydroxypropol-3-cyclodextrin are dissolved in a final concentration of 5% (w/v) (esmolol) or 7% and 0% (w/v) (hydroxypropyl-3-cyclodextrin) in water for injection purposes and stirred for 24 hours at room temperature.

Example 4

Example of Comparison

Production of a State-of-the-Art 5% Esmolol Solution for Injection

A parenteral solution was produced in accordance with the recipe set out in table 1.

TABLE 1

| Composition of the parenteral esmolol solution | |
|---|---|
| Substances | Quantity |
| Esmolol HCl | 500 mg |
| Sodium acetate | 34 mg |
| Glacial acetic acid | 3.674 mg |
| Propylene glycol | 518 mg |
| Ethanol | 402 mg |
| HCl or NaOH for pH 3.5-5.5 | q.s. |
| Water | ad 10 ml |

Example 5

Investigations of the Stability of Parenteral Esmolol Solutions

With solution described in examples 1 to 3, accelerated stability tests were carried out at a temperature of 75° C. After 0, 24, 45 and 70 hours samples were taken which were diluted with distilled water (20 µl sample+180 µl water). The accelerated breakdown was determined by HPLC as follows:

For the qualitative and quantitative analyses a Hitachi Elite LaChrom HPLC device with a diode array detector and a Waters Nova-Pak C18 4 µm 3.9×150 mm column were used. The mobile phase consisted of (A) $H_3PO_4$ (10 g/l) in water, adjusted to pH 2.35 with triethylamine (TEA) and (B) acetonitrile. The gradient used is set out in table 2.

TABLE 2

| HPLC method | | |
|---|---|---|
| Time (min) | A (%) | B (%) |
| 0 | 82 | 18 |
| 7 | 82 | 18 |
| 8 | 60 | 40 |
| 13 | 60 | 40 |
| 14 | 70 | 30 |
| 20 | 70 | 30 |
| 21 | 82 | 18 |
| 30 | 82 | 18 |

The flow rate was 1 ml/minute, the injection volume 20 µl. Esmolol hydrochloride was detected at 274 nm. The retention time of esmolol hydrochloride was on average 3.9 minutes, that of the principal degradation product ("contaminant A" in table 3 below) was 1.7 minutes. To determine degradation the ratio of the principal degradation product to remaining esmolol hydrochloride was calculate and indicated in percent ("degraded esmolol (%)").

The results of these studies show a decisively increased stability of the solutions containing cyclodextrin.

Figure 1:
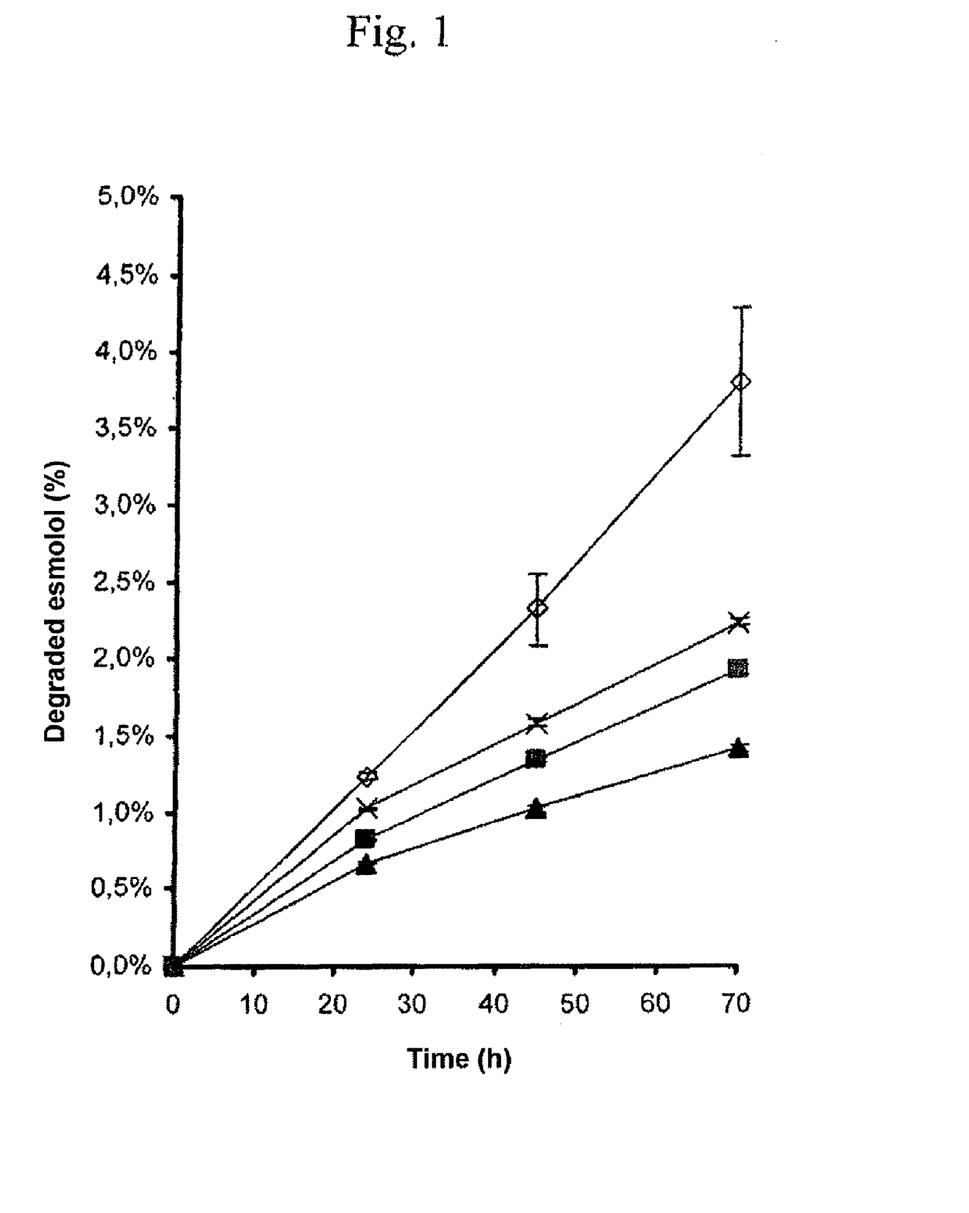
FIG. 1 shows the accelerated breakdown of a 5% esmolol reference solution and compositions according to the invention at 75° C.

FIG. 1 shows the accelerated degradation at 75° C. of the 5% esmolol reference solution and esmolol cycoldextrin complexes in water [(◇) 5% esmolol comparison solution with 0% cyclodextrin—example 3b; (X) 5% esmolol+γ-cyclodextrin—example 2b]; (■) 5% esmolol+(2-hydroxypropyl)-β-cyclodextrin—example 1); (▲) 5% esmolol+α-cyclodextrin—example 2a]. The values are mean values of 3 tests±SD.

Figure 2:
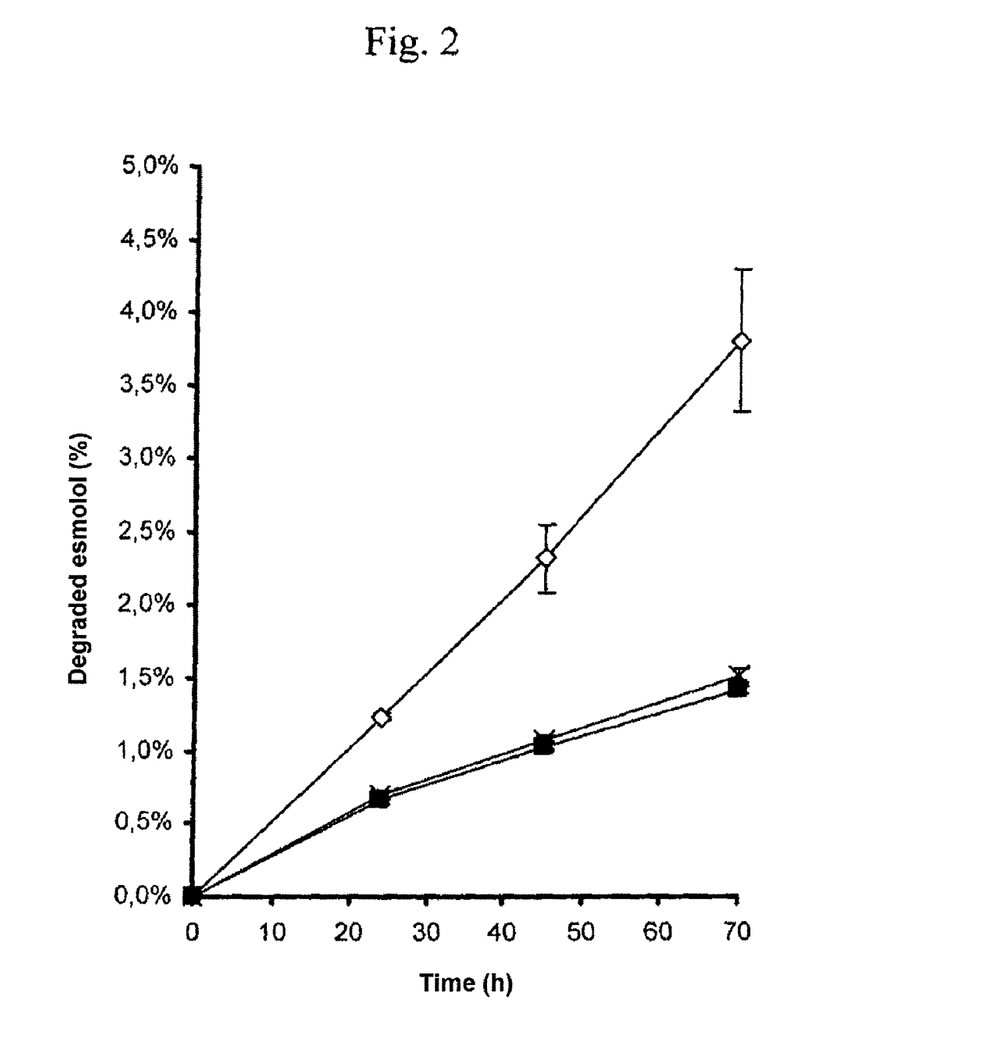
FIG. 2 shows the influence of freeze-drying on the accelerated breakdown of esmolol-cyclodextrin complexes in water at 75° C.

FIG. 2 shows the influence of freeze drying on the accelerated degradation of esmolol-cyclodextrin complexes in water at 75° C. [(◇) 5% esmolol comparison solution with 0% cyclodextrin—example 3b; (X) 5% esmolol in 14% α-cyclodextrin solution without freeze drying—example 3a; (■) 5% esmolol+α-cyclodextrin—example 2a with subsequent freeze drying and reconstitution in water]. The values are mean values of 3 tests±SD.

Figure 3:
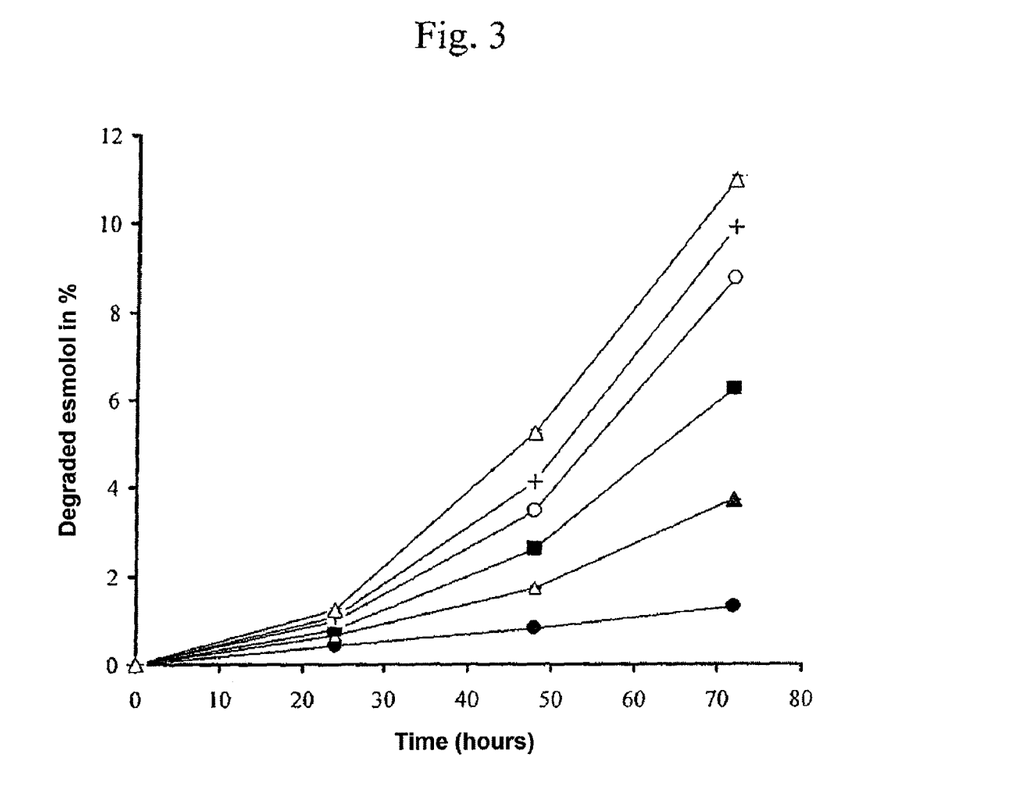
FIG. 3 shows the influence of the concentration of α-cyclodextrin on the stability of esmolol at 75° C.

FIG. 3 shows the influence of the concentration of α-cyclodextrin on the stability of an aqueous 5% esmolol solution at 75° C. [(Δ) 5% esmolol comparison solution with 0% α-cyclodextrin—example 3b; (+) 5% esmolol+1% α-cyclodextrin—in accordance with example 3b; (○) 5% esmolol+2% α-cyclodextrin—in accordance with example 3b; (■) 5% esmolol+4% α-cyclodextrin—in accordance with example 3b; (▲) 5% esmolol+7% α-cyclodextrin—in accordance with example 3b; (•) 5% esmolol+14% α-cyclodextrin—in accordance with example 3b;]. The values are mean values of 3 tests±SD.

Figure 4:
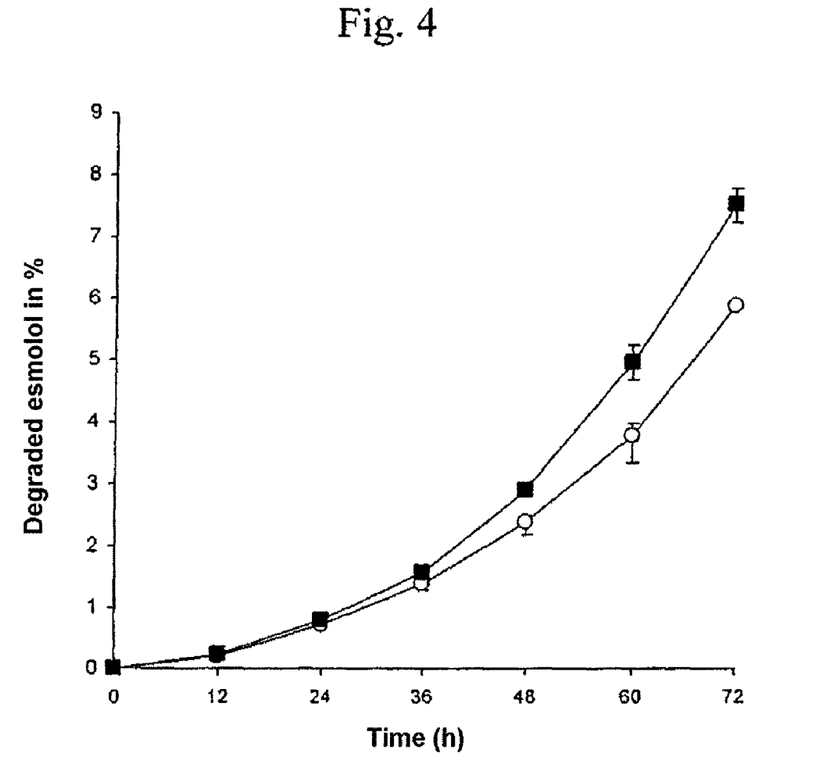
FIG. 4 shows the influence of hydroxypropyl-β-cyclodextrin on the stability of esmolol at 75° C.

FIG. 4 shows the influence of hydroxypopyl-β-cyclodextrin on the stability of an aqueous 5% esmolol solution at 75° C. [(■) 5% esmolol comparison solution with 0% hydroxypropyl-β-cyclodextrin—example 3c; (○) 5% esmolol+7% hydroxypropyl-β-cyclodextrin—in accordance with example 3c]. The values are mean values of 3 tests±SD.

Example 6

Storage Stability of Esmolol Cyclodextrin Complexes

Table 3 shows the storage stability of esmolol cyclodextrin complexes (example 3a) compared with a state-of-the-art formulation (example 4) on the basis of the increase in degradation products (=contaminants).

TABLE 3

Stability tests

| | Stability tests 25° C./60% r.h. Storage time | | | |
|---|---|---|---|---|
| | 0 months | 6 months | 0 months | 6 months |
| | Storage stability tests | | | |
| Contaminants | Esmolol formulation without cyclodextrin (example 4) | | Esmolol formulation with cyclodextrin (example 3a) | |
| CONTAMINANT A | 0 | 2.56 ± 0.53 | 0 | 1.94 ± 1.06 |
| CONTAMINANT B | n.d. | n.d. | n.d. | n.d. |
| CONTAMINANT C | n.d | n.d. | n.d. | n.d. |
| CONTAMINANT D | n.d. | .018 ± 0.01 | n.d. | n.d. |
| Unknown contaminants | 0 | 0.37 ± 0.04 | 0 | 0.38 ± 0.02 |
| Total | 0 | 3.11 | 0 | 2.24 |

Example 7

Determination of the Osmolarity

The osmolarity/reduction in freezing point vis-a-vis water was determined with a Knauer semi-micro-osmometer. In order to be able to determine the osmolarity with this osmometer the samples are cooled to freezing in the osmometer.

The 5% solution with α-cyclodextrin in accordance with example 3a has an osmolarity of 290 mosmol/l. This corresponds to an isotonic solution as the range of isotonia extends from 281 to 297 mosmol/l. Solutions of >310 mosmol/l would be described as hypertonic and solutions of <270 mosmol/l classified as hypotonic.

Example 8

Production and Stability Testing of Cyclodextrin-Landiolol Complexes

Figure 5:
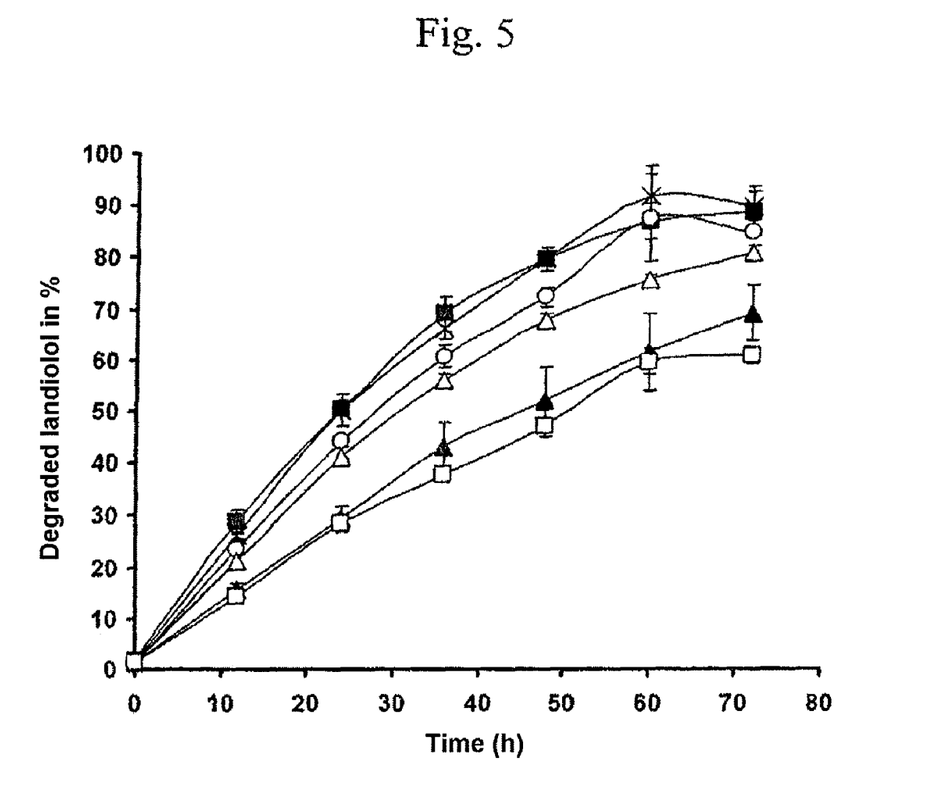
FIG. 5 shows the influence of α-cyclodextrin in increasing concentrations on the stability of landiolol in aqueous solution at 70° C.
Figure 6:
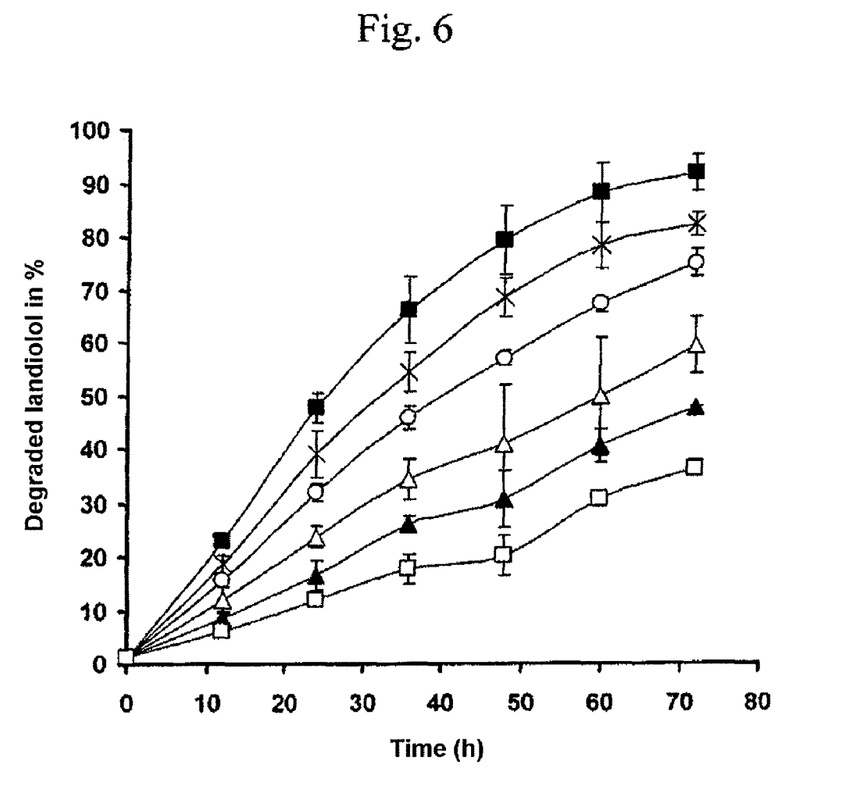
FIG. 6 shows the influence of 2-hydroxypropyl-β-cyclodextrin in increasing concentrations on the stability of landiolol in aqueous solution at 70° C.
Figure 7:
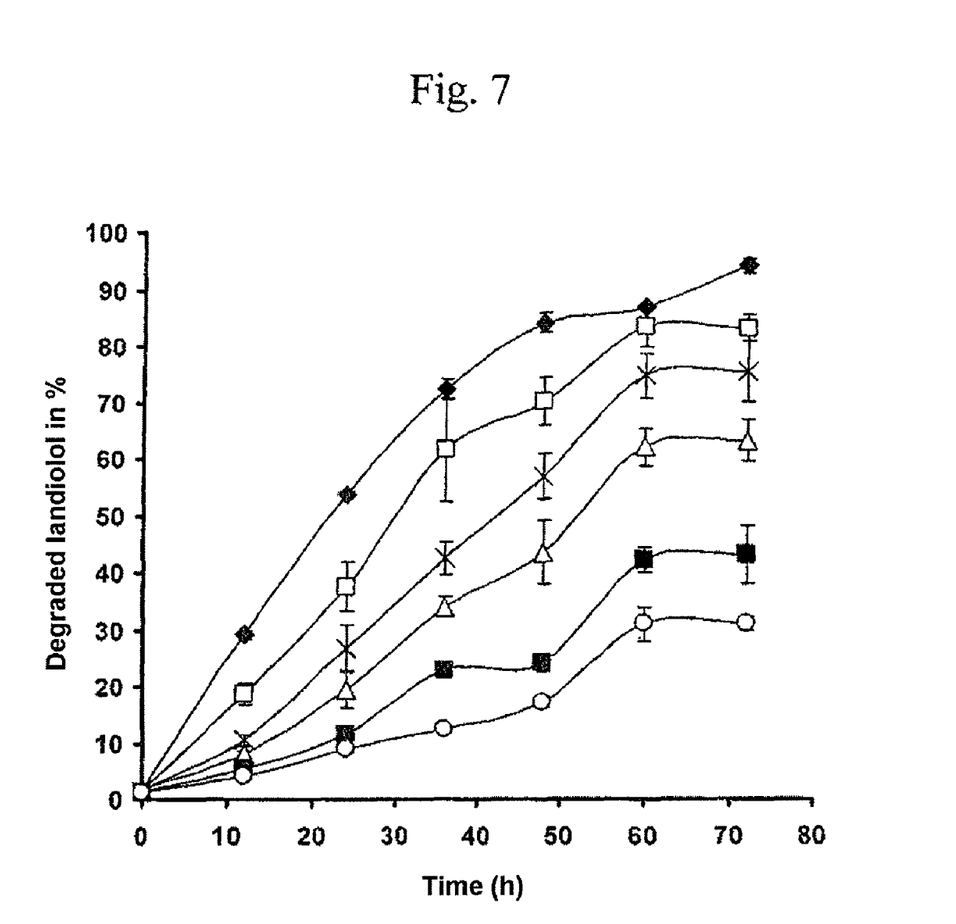
FIG. 7 shows the influence of γ-cyclodextrin in increasing concentrations on the stability of landiolol in aqueous solution at 70° C.

Landiolol was dissolved in purified water at a concentration of 0.25% (m/v). Subsequently α-cyclodextrin (Cyclolab, Budapest), 2-hydroxypropyl-β-cyclodextrin (CTD, Inc., Florida) and γ-cyclodextrin (ISP, Germany) was added in final concentrations of 0%, 0.5%, 1%, 2% and 7% (w/v). The solutions were heated to 70° C. and the stability of landiolol determined in accordance with the HPLC method described in example 5. Landiolol was detected at 220 nm. The retention time of landiolol hydrochloride was on average 10.5 minutes, that of the principal degradation product 1.4 minutes. To determine the degradation the ratio of the principal degradation product to the remaining landiolol hydrochloride was calculated and indicated in percent ("degraded landiolol (%)"). The results of this study are shown in FIG. 5-7. The shown values are mean values of 3 tests±SD. FIG. 5 shows the influence of 0% (■), 0.5% (X), 1% (○), 2% (Δ), 4% (▲) and 7% (□) α-cyclodextrin on the stability of landiolol at 70° C.

FIG. 6 shows the influence of 0% (■), 0.5% (X), 1% (○), 2% (Δ), 4% (▲) and 7% (□) hydroxypropyl-β-cyclodextrin on the stability of landiolol at 70° C.

FIG. 7 shows the influence of 0% (♦), 0.5% (□), 1% (X), 2% (Δ), 4% (■) and 7% (○) γ-cyclodextrin on the stability of landiolol at 70° C.

Example 9

Evaluation of the Influence of the pH Value on the Stability of Landiolol

Figure 8:
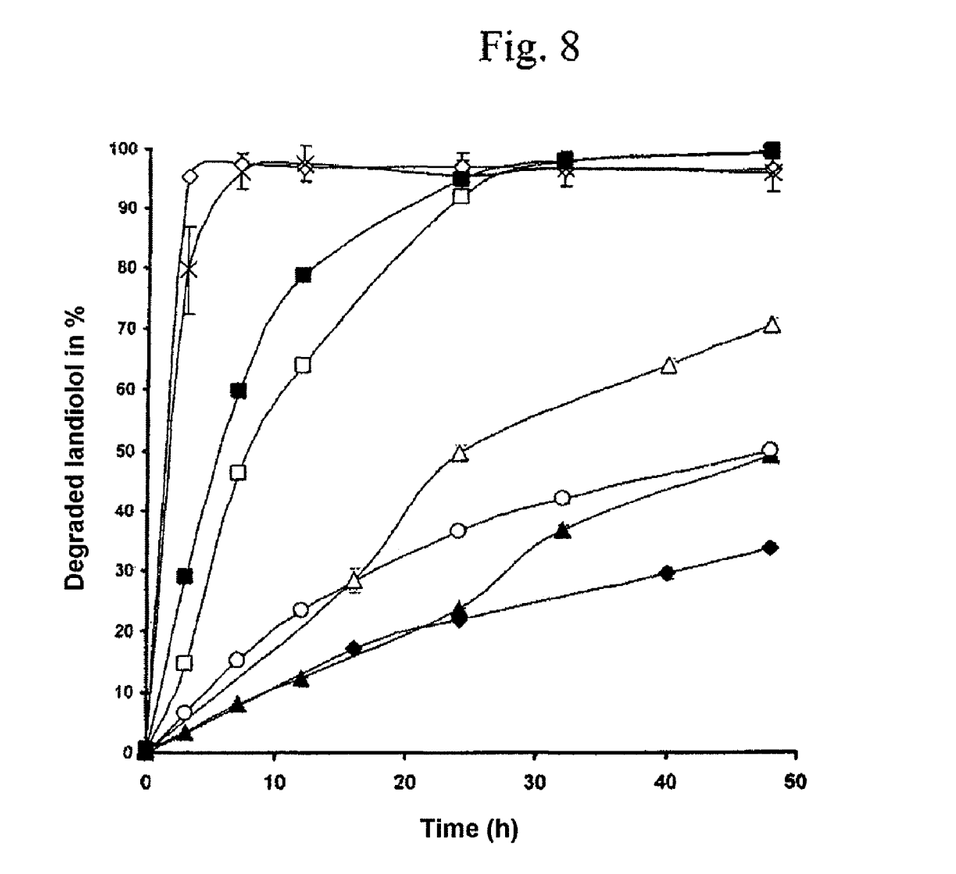
FIG. 8 shows the influence of the pH value on the stability of landiolol in aqueous solution at 70° C.

Landiolol was dissolved in purified water at a concentration of 0.25 (w/v). The pH value was then adjusted to 3; 4; 5; 5.5; 6; 6.5; 7 and 8. The solutions were heated to 70° C. and the stability of landiolol determined with the HPLC method described in examples 5 and 8. The results of these studies are shown in FIG. 8. These show the degradation of landiolol at pH 3.0 (◇), pH 4.0 (X), pH 5.0 (□), pH 5.5 (Δ), ph 6.0 (◇), pH 6.5 (♦), pH 7.0 (○) and pH 8.0 (■). The shown values are mean values of 3 tests±SD.

Example 10

Figure 9:
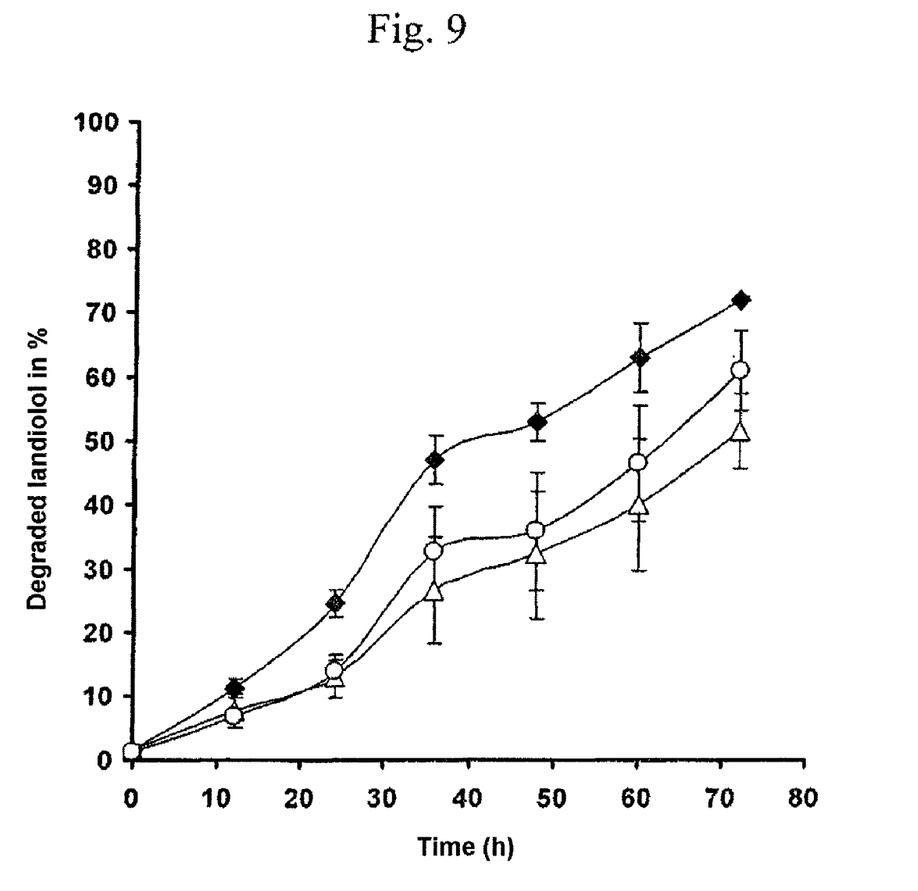
FIG. 9 shows the influence of cyclodextrins (2%, w/v) in which landiolol was stored by means of concentrated suspensions on the stability of aqueous landiolol solutions of 0.25% (w/v) at 70° C.

Stability Tests of Cyclodextrin-Landiolol Complexes Produced by Means of Concentrated Suspensions Landiolol and α-cyclodextrin (Cyclolab, Budapest), 2-hydroxypropyl-β-cyclodextrin (CTD Inc., Florida) or γ-cyclodextrin (ISP, Germany) were suspended in purified water in a concentration of 10% landiolol (w/v) and 80% cyclodextrin (w/v) and stirred for two hours at room temperature. After 5 minutes of ultrasound treatment the suspensions were diluted in stages so that the final concentration of landiolol was 0.25% (w/v). These solutions were incubated at 70° C. and the taken sample were analysed by means of the HPLC method described in examples 5 and 8. The results of this study are set out in FIG. 9. These show the influence of 2% α-cyclodextrin (▲), 2% 2-hydroxypropyl-β-cyclodextrin (Δ) and 2% γ-cyclodextrin (○) on the stability of landiolol at 70° C. The shown values are mean values of 3 tests±SD.

Example 11

Vasoprotective Effect of Cyclodextrin on Intravenously Administered Ultrashort-Effect β-Adrenoceptor Antagonists Solutions of said β-adrenoreceptor antagonists with or without cyclodextrin were chronically infused into rats via the jugular vein for a longer period. It can be seen that said beta-adreno-receptor antagonists in solutions containing cyclodextrin bring about considerably less endothelial and vascular damage than the use of a conventional solution.

What is claimed:
1. A pharmaceutical composition comprising:
   a) landiolol or a pharmaceutically acceptable salt thereof at a concentration from 0.005 to 0.5% (w/v);
   b) water; and
   c) 2-hydroxypropyl-β-cyclodextrin at a concentration from 0.5 to 7% (w/v).

2. The pharmaceutical composition of claim 1, wherein the pH value of the composition is 3 to 7.5.
3. The pharmaceutical composition of claim 2, wherein the pH value of the composition is 5 to 7.
4. The pharmaceutical composition of claim 1, wherein the concentration of 2-hydroxypropyl-β-cyclodextrin is 0.5 to 5% (w/v).
5. The pharmaceutical composition of claim 1, wherein the concentration of landiolol or the pharmaceutically acceptable salt thereof is 0.25%.
6. The pharmaceutical composition of claim 1, wherein the composition has an osmolarity of 270 mosmol/l to 310 mosmol/l.
7. The pharmaceutical composition of claim 6, wherein the composition has an osmolarity of 280 mosmol/l to 300 mosmol/l.
8. The pharmaceutical composition of claim 1, wherein the composition is present in the form of a sales unit selected from the group consisting of: a 1 ml solution containing 5-20 mg landiolol or a pharmaceutically acceptable salt thereof, a 2 ml solution containing 5-100 mg landiolol or a pharmaceutically acceptable salt thereof, a 5 ml solution containing 10-500 mg landiolol or a pharmaceutically acceptable salt thereof, a 10 ml solution containing 10-5000 mg landiolol or a pharmaceutically acceptable salt thereof, a 25 ml solution containing 25-2500 mg landiolol or a pharmaceutically acceptable salt thereof, a 50 ml solution containing 50-5000 mg landiolol or a pharmaceutically acceptable salt thereof, a 100 ml solution containing 50-5000 mg landiolol or a pharmaceutically acceptable salt thereof, and a 250 ml solution containing 50-5000 mg landiolol or a pharmaceutically acceptable salt thereof.

* * * * *